(12) United States Patent
Ushiki et al.

(10) Patent No.: US 7,700,380 B2
(45) Date of Patent: *Apr. 20, 2010

(54) SURFACE CONTAMINATION ANALYZER FOR SEMICONDUCTOR WAFERS, METHOD USED THEREIN AND PROCESS FOR FABRICATING SEMICONDUCTOR DEVICE

(75) Inventors: Takeo Ushiki, Tokyo (JP); Keizo Yamada, Tokyo (JP); Yohsuke Itagaki, Tokyo (JP); Tohru Tsujide, Tokyo (JP)

(73) Assignee: Topcon Corporation, Itabashi-Ku, Tokyo (JP)

(*) Notice: Subject to any disclaimer, the term of this patent is extended or adjusted under 35 U.S.C. 154(b) by 1296 days.

This patent is subject to a terminal disclaimer.

(21) Appl. No.: 11/151,068

(22) Filed: Jun. 13, 2005

(65) Prior Publication Data

US 2005/0230622 A1    Oct. 20, 2005

Related U.S. Application Data

(62) Division of application No. 10/831,851, filed on Apr. 26, 2004, now Pat. No. 6,943,043, which is a division of application No. 10/083,440, filed on Feb. 26, 2002, now Pat. No. 6,753,194.

(30) Foreign Application Priority Data

Mar. 2, 2001    (JP) ............................... 2001-58075

(51) Int. Cl.
      *H01L 21/66*    (2006.01)
(52) U.S. Cl. .......................... 438/14; 250/306; 250/310
(58) Field of Classification Search .................. None
      See application file for complete search history.

(56) References Cited

U.S. PATENT DOCUMENTS

| | | | |
|---|---|---|---|
| 3,614,608 A | 10/1971 | Giedd | |
| 4,949,162 A | 8/1990 | Tamaki et al. | |
| 4,980,639 A | 12/1990 | Yoshizawa et al. | |
| 4,988,877 A | 1/1991 | Stokowksi et al. | |
| 5,001,536 A | 3/1991 | Fukuzawa et al. | |
| 5,089,774 A | 2/1992 | Nakano | |
| 5,132,507 A | 7/1992 | Nakano | |
| 5,162,241 A * | 11/1992 | Mori et al. | ............ 438/402 |
| 5,280,176 A | 1/1994 | Jach et al. | |
| 5,327,012 A | 7/1994 | Yano et al. | |
| 5,365,034 A | 11/1994 | Kawamura et al. | |
| 5,412,210 A | 5/1995 | Todokoro et al. | |
| 5,453,994 A | 9/1995 | Kawamoto et al. | |
| 5,481,109 A | 1/1996 | Ninomiya et al. | |
| 5,493,236 A | 2/1996 | Ishii et al. | |
| 5,614,833 A | 3/1997 | Golladay | |
| 5,637,186 A | 6/1997 | Liu et al. | |
| 5,757,198 A | 5/1998 | Shida et al. | |
| 5,780,870 A | 7/1998 | Maeda et al. | |
| 5,781,017 A | 7/1998 | Cole et al. | |
| 5,801,540 A | 9/1998 | Sakaguchi | |
| 5,815,002 A | 9/1998 | Nikawa | |
| 5,900,645 A | 5/1999 | Yamada | |
| 5,903,011 A | 5/1999 | Hatanaka | |
| 5,989,919 A | 11/1999 | Aoki | |
| 6,037,588 A | 3/2000 | Liu et al. | |
| 6,127,193 A | 10/2000 | Bang et al. | |
| 6,294,919 B1 | 9/2001 | Baumgart | |
| 6,317,514 B1 | 11/2001 | Reinhorn et al. | |
| 6,356,347 B1 * | 3/2002 | Watanabe et al. | ............ 356/369 |
| 6,407,386 B1 | 6/2002 | Dotan et al. | |
| 6,417,680 B1 | 7/2002 | Birdsley et al. | |
| 6,603,122 B2 | 8/2003 | Taleyarkhan | |
| 2002/0148975 A1 | 10/2002 | Kimba et al. | |

FOREIGN PATENT DOCUMENTS

| | | |
|---|---|---|
| JP | 50-63990 | 5/1975 |
| JP | 57-6310 | 1/1982 |
| JP | 62-19707 | 1/1987 |
| JP | 63-9807 | 1/1988 |
| JP | 03-205573 | 9/1991 |
| JP | 04-062857 | 2/1992 |
| JP | 06-273297 | 9/1994 |
| JP | 07-066172 | 3/1995 |
| JP | 07-221148 | 8/1995 |
| JP | 08-005528 | 1/1996 |
| JP | 08-313244 | 11/1996 |
| JP | 09-061142 | 3/1997 |
| JP | 09-243535 | 9/1997 |
| JP | 10-281745 | 10/1998 |
| JP | 10-281746 | 10/1998 |
| JP | 10-300450 | 11/1998 |
| JP | 11-026343 | 1/1999 |
| JP | 2000-124276 | 4/2000 |
| JP | 2000-164715 | 6/2000 |
| JP | 2000-174077 | 6/2000 |
| JP | 2000-180143 | 6/2000 |

OTHER PUBLICATIONS

"An In-Line Contact and Via Hole Inspection Method Using Electron Beam Compensation Current", Yamada et al., IEEE 1999, Doc. No. 0-7803-5413-3/99/, available from http://www.fabsol.com/us/images/library/21.pdf.

Office Action issued on Nov. 6, 2009 in U.S. Appl. No. 12/248,312.

* cited by examiner

*Primary Examiner*—Marjorie Moran
*Assistant Examiner*—Jason M Sims
(74) *Attorney, Agent, or Firm*—Buchanan Ingersoll & Rooney PC (57) ABSTRACT

A semiconductor wafer is radiated with an electron beam so that the inelastic scattering takes place in the narrow region, and current flows out from the narrow region; the amount of current is dependent on the substance or substances in the narrow region so that the analyst evaluates the degree of contamination on the basis of the substance or substances specified in the narrow region.

13 Claims, 9 Drawing Sheets

SURFACE CONTAMINATION ANALYZER FOR SEMICONDUCTOR WAFERS, METHOD USED THEREIN AND PROCESS FOR FABRICATING SEMICONDUCTOR DEVICE

RELATED APPLICATIONS

This application is a divisional of application Ser. No. 10/831,851 filed 04/26/2004 now U.S. Pat. No. 6,943,043, which is a divisional of application Ser. No. 10/083,440 (now U.S. Pat. No. 6,753,194), filed Feb. 26, 2002, which claims benefit of priority under 35 U.S.C. § 119 to Japanese Patent Application No. 2001-58075, filed on Mar. 2, 2001.

FIELD OF THE INVENTION

This invention relates to fabrication technologies for semiconductor devices and, more particularly, to a surface contamination analyzer for semiconductor wafers, a method used therein and a process for fabricating a semiconductor device.

DESCRIPTION OF THE RELATED ART

Semiconductor devices have been enhanced in integration density, and, accordingly, miniature circuit components are integrated on the small semiconductor chip. If the surface of a semiconductor wafer is contaminated with trace elements, the miniature circuit components are much liable to be damaged, and the production yield is lowered. Research and development efforts are being made on 1 giga-bit DRAM (Dynamic Random Access Memory). The contamination due to the trace elements is serious in the process for fabricating the DRAMs. Of course, miniaturization is the key technologies in the development. A cleaning technology is also important for the highly reliable ultra large scale integration devices. In fact, the requirement for an ultra clean surface is getting severe and severe.

Organic compounds in the clean room and plasticizer in the wafer cassette are presently seemed to be origins of the contaminants. The organic contaminants are adhered to the surfaces of the semiconductor wafers in the form of molecules and/or cluster, and are causative of reduction in production yield. A particle of organic compound is assumed to be adhered to the surface of a semiconductor wafer. The organic compound particle is an obstacle in the removal of natural oxide. Even though the manufacturer exposes the surface of the semiconductor wafer through the removal of the natural oxide before the deposition of metal, the organic compound particle does not allow the etchant to remove the natural oxide therebeneath. This means that a part of the metal layer is held in contact with the residual natural oxide on the surface of the semiconductor wafer. Although the resistance in the direct contact between the metal layer and the semiconductor wafer is fallen within a target range, the contact resistance is locally increased, and uniform contact resistance is not achieved.

Organic contaminant particles are assumed to be adhered to a surface of semiconductor wafer. Dopant impurity may be ion implanted into the surface of the semiconductor wafer/semiconductor layer. The organic contaminant particles are also obstacle against the ion-implantation, and do not allow the impurity region to have a target impurity profile. If the impurity region is used for a channel region or diode, the field effect transistor or diode does not exhibit designed characteristics. Especially, the channel region forms a part of flash memory. Electrons or holes are injected and evacuated through the gate oxide layer between the channel region and the floating electrode. The residual organic contaminant particles accelerate the aged deterioration, and, accordingly, reduce the duration of life as reported by Toshiyuki Iwamoto in "Research for Highly Reliable Extremely Thin Oxide Layer", dissertation for a doctor degree, Tohoku University, March, 1998.

Semiconductor wafers are concurrently conveyed from an apparatus to another as a lot. Since the time period consumed in an apparatus is different from the time period consumed in another apparatus, the semiconductor wafers are to wait until the previous lot is unloaded from the apparatus, and are exposed to the atmosphere in the clean room. While the semiconductor wafers are being exposed to the atmosphere, the molecular contaminants or contaminant clusters are unavoidably adhered to the surfaces of the semiconductor wafers. The waiting time is different between the lots, and, accordingly, the semiconductor wafers are different in degree of contamination from one another. The contaminants are influential in the electric properties of the semiconductor wafers. Thus, accurate evaluation technologies are required for the ultra large-scale integration devices.

A wide variety of material is used in the processes for fabricating the ultra large-scale integration devices. Silicon dioxide, i.e., $SiO_2$ is popular to the semiconductor device manufacturers. Other kinds of insulating material such as, for example, SiOF, HSQ, SiN and $Ta_2O_5$ are employed in the ultra large-scale integration devices. Semiconductor wafers are cleaned in certain cleaning solution such as water solution containing sulfuric acid and hydrogen peroxide or water solution containing ammonia and hydrogen peroxide. The contaminants are removed through chemical reactions with these kinds of cleaning solution. However, new cleaning technologies are required for the new kinds of material. Physical phenomena are employed in the cleaning technologies for those kinds of material. The contaminants are, by way of example, removed from semiconductor wafers by using mega-sonic or ultra sonic. These cleaning technologies are effective against contaminants on the surfaces of the semiconductor wafers. However, the cleaning solution and/or the physical energy hardly reaches the contaminants in deep valleys or trenches and micro-holes formed in the three-dimensional structure. If the contaminants are left on the bottom surfaces of the trenches and micro-holes, the residual contaminants vary the electric properties, and the circuit components formed in the trenches and micro-holes do not exhibit designed characteristics. The defective circuit components are causative of reduction in production yield. Even though the products pass the inspections, malfunction is liable to take place in the products, and, accordingly, those products are less reliable.

In order to cope with the contamination, it is necessary to evaluate the surface contamination without any damage to the complicated surface configuration for optimizing the cleanings. A total reflection fluorescent x-ray spectroscopy has been developed for the surface evaluation. The total reflection fluorescent x-ray spectroscopy is usually abbreviated as "TXRF". Monochromatic x-ray is radiated to the surface of a semiconductor wafer at a small incident angle. The semiconductor wafer and contaminants generate fluorescent x-ray to a semiconductor detecting unit, and the contaminants are specified on the basis of the fluorescent x-ray incident onto the semiconductor detecting unit. Metal contaminants are well detected through the total reflection fluorescent x-ray spectroscopy. However, contaminants essentially composed of carbon-containing/nitrogen-containing molecules are hardly detected through the total reflection fluorescent x-ray spectroscopy. Moreover, the mono-chromatic x-ray does not reach the bottom surfaces of extremely deep trenches, because the incident angle is small, and the contaminants on the bottom surfaces are not detectable.

A surface contamination analyzer with an optical detector is disclosed in Japanese Patent Application laid-open No. 7-221148. Infrared light is radiated from a light source to the surface of a semiconductor wafer, and the reflected infrared light is incident on the surface at a predetermined angle. The infrared light is reflected on the surface, again, and the reflection is analyzed through a spectral analysis. The contaminants essentially composed of carbon-containing/nitrogen-containing molecules are detected without serious damage to the semiconductor wafer.

Another prior art surface contamination analyzer is disclosed in Japanese Patent Application laid-open No. 9-243535. Carrier gas flows over the surface of a semiconductor wafer, and laser light is radiated onto a certain area of the surface. The contaminants are vaporized in the radiation of the laser light, and the gaseous contaminant is ionized together with the carrier gas. The ionized gas is analyzed through a mass spectrometry, and the contaminants are specified on the basis of the analysis result. Even if the contaminants are on the bottom surfaces of the extremely deep trenches, the laser light reaches the contaminants so as to vaporize them. Thus, the contaminants in the extremely deep trenches are analyzable through the second prior art surface contamination analysis.

A problem inherent is encountered in the first prior art surface contamination analysis technology in a small signal-to-noise ratio of the reflection from the trenches/holes with large aspect ratios. This is because of the fact that the first prior art surface contamination analyzer is to keep the incident light at the predetermined angle. In other words, the limit is set on the incident angle in the surface contamination analysis so that the reflected infrared light does not reach the bottoms of the trenches/holes with the large aspect ratios.

On the other hand, a problem inherent in the second prior art surface contamination analyzer is a small signal-to-noise ratio of the vapor generated from an extremely narrow area. When the vapor is generated from a relatively wide area, a large amount of contaminants is vaporized, and the mass spectrometry is surely reliable. However, the amount of contaminants vaporized from an extremely narrow area is too little to analyze it through the mass spectrometry. Thus, the second prior art surface contamination analyzer is not available for a detailed report.

If the analysis on the surface contamination is inaccurate, it is difficult to optimize the cleaning against the contamination, and the residual contaminants are carried from an apparatus to another through the contaminated semiconductor wafer. This results in reduction in production yield and poor reliability of semiconductor devices. The surface contamination analysis is an important step in the process for fabricating a semiconductor device.

SUMMARY OF THE INVENTION

It is therefore an important object of the present invention to provide a surface contaminant analyzer, which is available for a detailed report on a surface contamination with carbon, nitrogen-containing molecules or cluster regardless of the surface configuration of a specimen.

It is also an important object of the present invention to provide an analyzing method used in the surface contamination analyzer.

It is another important object of the present invention to provide a process for fabricating a semiconductor device through which the production yield and reliability of semiconductor device are enhanced.

In accordance with one aspect of the present invention, there is provided a surface contamination analyzer comprising an electron beam radiating unit including an electron gun for radiating an electron beam along a certain path, and a current measuring unit including a wall defining a chamber into which the certain path extends, a movable stage mounting a sample and moved so as to align a target region with the certain path and a current measuring equipment electrically connected between the sample and a constant voltage source for measuring the amount of current flowing out from the target region under the radiation of the electron beam onto the target region.

In accordance with another aspect of the present invention, there is provided a method for investigating a degree of contamination on a target region of a contaminated sample comprising the steps of a) aligning the target region of the contaminated sample with a path of an electron beam, b) measuring the amount of current flowing out from the target region under radiation of the electron beam, c) comparing the amount of current with the amount of reference current flowing out from a region of a reference sample corresponding to the contaminated sample for determining a difference between the amount of current measured and the amount of reference current, and d) determining the degree of contamination on the target region on the basis of the difference.

In accordance with yet another aspect of the present invention, there is provided a process for fabricating a semiconductor device comprising the steps of a) treating the semiconductor wafer in an atmosphere potentially having an origin of contamination, b) investigating a degree of contamination on the semiconductor wafer through sub-steps of b-1) aligning a target region of the semiconductor wafer with a path of an electron beam, b-2) measuring the amount of current flowing out from the target region under radiation of the electron beam, b-3) comparing the amount of current with the amount of reference current flowing out from a region of a reference wafer corresponding to the semiconductor wafer for determining a difference between the amount of current measured and the amount of reference current and b-4) determining the degree of contamination on the semiconductor wafer on the basis of the difference, c) evaluating the degree of contamination to see whether or not a cleaning is required for the semiconductor wafer, d) decontaminating the semiconductor wafer when the answer at step c) is given affirmative and e) treating the semiconductor wafer in another next atmosphere.

BRIEF DESCRIPTION OF THE DRAWINGS

The features and advantages of the surface contamination analyzer, method and the process for fabricating a semiconductor device will be more clearly understood from the following description taken in conjunction with the accompanying drawings in which.

DESCRIPTION OF THE PREFERRED EMBODIMENTS

According to the present invention, an electron beam is radiated onto a target substrate and a reference substrate the surface state of which has been already known. The electron beam gives rise to current flowing through the target substrate and the reference substrate to a constant voltage source. The amount of current flowing through the target substrate is compared with the amount of current flowing through the reference substrate, and the surface contamination of the target substrate is evaluated on the basis of the difference therebetween.

Assuming now an narrow target area is contaminated with chemical molecules or cluster, the electron beam radiation gives rise to continuous inelastic scattering in the chemical molecules/cluster as well as the substrate. The primary electron looses part of the energy, and part of the excited electron does not reach the surface of the substrate. The atoms are partially ionized. For this reason, the electric charges do not balance in the bulk, i.e., the chemical molecules/cluster and the substance forming the substrate. In order to recover the balance, the current flows through the substrate. The current is called as "absorption current". The amount of current is strongly dependent on the electron scattering in the material forming the substrate. This is because of the fact that the band gap is different from each other. Semiconductors have band gaps wider than those of metals and narrower than those of insulators. In metal, the secondary electrons are much liable to exceed the forbidden band, and lose the energy through the interaction with the electrons in the lattice. On the other hand, the interaction hardly takes place in the insulator, because the forbidden band is wide. In other words, the electrons are less liable to lose the energy loss. Thus, the amount of current is varied depending upon the material radiated with the electron beam. Accordingly, the material is specified by comparing the amount of current measured with those of reference substrate. It is preferable to radiate the electron beam for a long time. The current is generated for the long time, and the amount of current is accumulated in the same period. The difference becomes large, and the substance in the target region becomes clearly discriminative.

As will be understood, the electron beam is radiated onto the narrow area on the substrate at a predetermined acceleration energy. The electron beam causes the electron scattering to take place in the surface portion of the order of tens nanometers thick, which is equal to the mean range of the electron beam. If a piece of hydrocarbon compound, which is electrically insulating, is adhered to the surface of the substrate, the absorption current is different in amount from that flowing through the substrate without any hydrocarbon compound. The surface state of the substrate is evaluated on the basis of the difference in the amount of absorption current.

There is not any limit on the incident angle of the electron beam. Even if a contact hole with a large aspect ratio is formed in the surface portion of the substrate, the electron beam reaches the bottom of the contact hole by adjusting the incident angle to a large value. The absorption current flows out through the reverse surface of the substrate. The signal-to-noise ratio is large enough to analyze the material exactly.

In another embodiment, the electron beam is radiated at an angle so as to measure the amount of current, and electron beam radiation is repeated at different angles so as to measure the amount of current in each electron beam radiation. In this instance, the amount of current flowing through the target substrate at each angle is compared with the amount of current flowing through the reference substrate at the same angle. The surface contamination is accurately evaluated through the multiple comparison.

In yet another embodiment, the target substrate is treated with heat in inert gas prior to the radiation with the electron beam, and the surface contamination is evaluated as described hereinbefore. The heat treatment may be repeated at different temperatures so as to measure the amount of current after each heat treatment. The accuracy of the evaluation is enhanced.

In still another embodiment, the electron beam is accelerated at a certain value of the acceleration energy, and the electron beam radiation is repeated at different values of the acceleration energy. The amount of current is measured at each electron beam radiation, and is compared with that measured through the reference substrate.

According to the present invention, surface contamination analyzers each comprise current measuring units and electron beam radiating units. The current measuring unit has a movable stage in a chamber thereof and an ampere meter, and the target substrate and the reference substrate are placed on the movable stage. The relative position between the target/reference substrates and the electron beam radiating unit is varied by means of the movable stage. The target substrate and the reference substrate are electrically connected in parallel to the constant voltage source such as, for example, the ground. The electron beam radiating unit radiates an electron beam onto the target substrate and the reference substrate placed on the movable stage. The electron beam is focused on a narrow target area on the surface of the target/reference substrate. Then, current flows to the constant voltage source, and the amount of current is measured by means of the ampere meter.

In a surface contamination analyzer implementing one of the embodiments, the movable stage is inclined with respect to the virtual surface where the target/reference substrates are moved relatively to the electron beam. The radiation angle is varied by inclining the target/reference substrates.

The surface contamination analysis forms at least one step in a process for fabricating semiconductor devices. Various treatments such as, for example, diffusion, oxidation, deposition and ion-implantation are selectively carried out on a semiconductor wafer at different steps of the fabrication process. When the semiconductor wafer reaches the step of evaluating the surface state of the semiconductor wafer, the semiconductor wafer is placed on the movable stage as the target substrate. The surface contamination is investigated as described hereinbefore, and the result is evaluated to see whether or not a cleaning step is required for the steps to be carried out. If the surface contamination is serious, the semiconductor wafer is cleaned before proceeding to the next step. On the other hand, when the surface contamination is negligible, the semiconductor wafer proceeds to the next step.

Plural sorts of cleaning step may be prepared for the semiconductor wafer, and is selectively carried out depending upon the evaluation result.

First Embodiment

Figure 1:
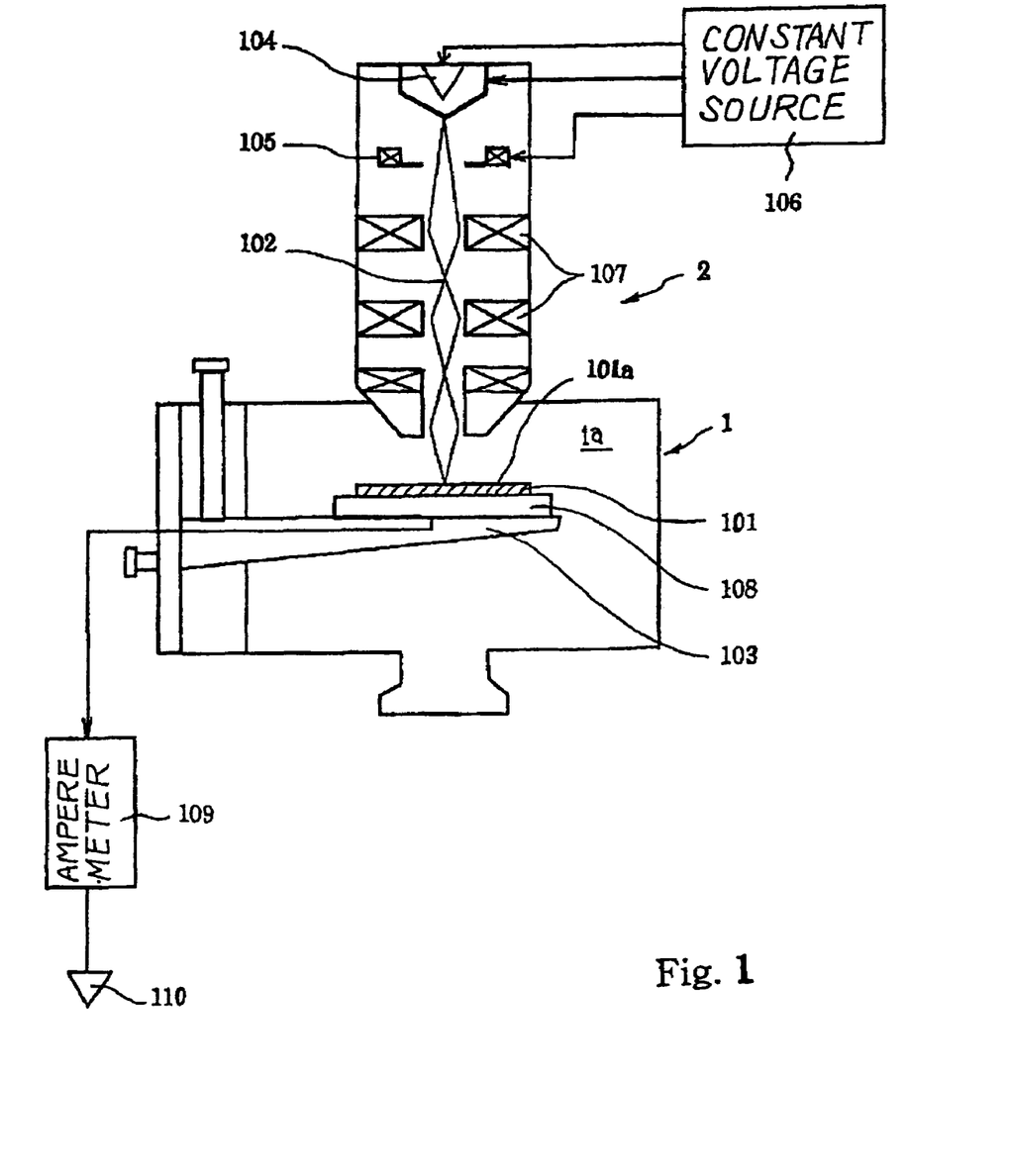
FIG. 1 is a schematic view showing the arrangement of a surface contamination analyzer according to the present invention.

Referring to FIG. 1 of the drawings, a surface contamination analyzer embodying the present invention largely comprises a current measuring unit 1 and an electron beam radiating unit 2. The current measuring unit 1 is formed with a chamber, and the electron beam radiating unit 2 projects into the chamber. A target such as, for example, a semiconductor wafer 101 is placed in the current measuring unit 1, and is grounded. The electron beam 102 is radiated from the electron beam radiating unit 2 onto the semiconductor wafer 101. The semiconductor wafer 101 is on the way to the end of a process for fabricating semiconductor devices, and a major surface 101a of the semiconductor wafer 101 is rough due to trenches, contact holes and lower-level wiring layers. The electron beam 102 is so thin that bottom surfaces of the valleys are radiated with the thin electron beam 102.

The current measuring unit 1 is formed with a chamber 1a, and a movable stage 103 is provided in the chamber 1a. The movable stage 103 is movable on a virtual plane perpendicular to the electron beam 102. A narrow area to be radiated with the electron beam is specified in an orthogonal coordinate system or a polar coordinate system. The stage 103 is movable in the two directions perpendicular to each other or in both of the direction of radius vector and the angle. The semiconductor wafer 101a is placed on the movable stage 103, and the movable stage 103 aligns the target region with the electron beam 102.

The current measuring unit 1 further comprises a collecting electrode 108 and an ampere meter 109. The collecting electrode 108 is inserted between the movable stage 103 and the semiconductor wafer 101, and is connected through the ampere meter 109 to the ground 110. The connection between the collecting electrode 108 and the ampere meter 109 is only one current path so that the absorption current does not flow into the other component such as the movable stage 103.

The electron beam radiating unit 2 comprises an electron gun 104, an anode 105, a constant voltage source 106 and an electron lens 107. The electron gun 104 is powered by the constant voltage source 106, and radiates the electron beam 102 toward the movable stage 103. The anode 105 is appropriately biased by the constant voltage source 106, and accelerates the electron beam 102. The electron lens 107 is provided between the electron gun 104 and the semiconductor wafer 101 on the movable stage 103, and controls the amount of current of the electron beam 102 and the convergence of the electron beam 102.

When the surface contamination in a target region of the semiconductor wafer 101 is to be investigated, the semiconductor wafer 101 is placed on the collecting electrode 108, and the movable stage 103 makes the target region aligned with path through which the electron beam 102 is radiated. The electron beam 102 is radiated from the electron gun 104, and is accelerated in the electric field created by the anode 105. The electron beam 102 is converged by the electron lens 107, and is incident onto the target region on the major surface 101a. The electron scattering takes place in the target region, and the current flows into the collecting electrode 108. The current flows from the collecting electrode 108 through the ampere meter 109 into the ground 110. The electron beam radiation is continued for a certain time period, and the value of current is accumulated in the ampere meter 109. The accumulated value is unique to a contaminant so that the analyst specifies the contaminant on the basis of the accumulated value.

The present inventors carried out the following experiment, and confirmed that the surface contamination was accurately evaluated through the surface contamination analysis according to the present invention.

First, the inventors prepared two silicon wafers. The diameter of the silicon wafers was 200 millimeters. The silicon wafers were p-conductivity type, and the resistivity was of the order of 1 ohm-cm.

Figure 2:
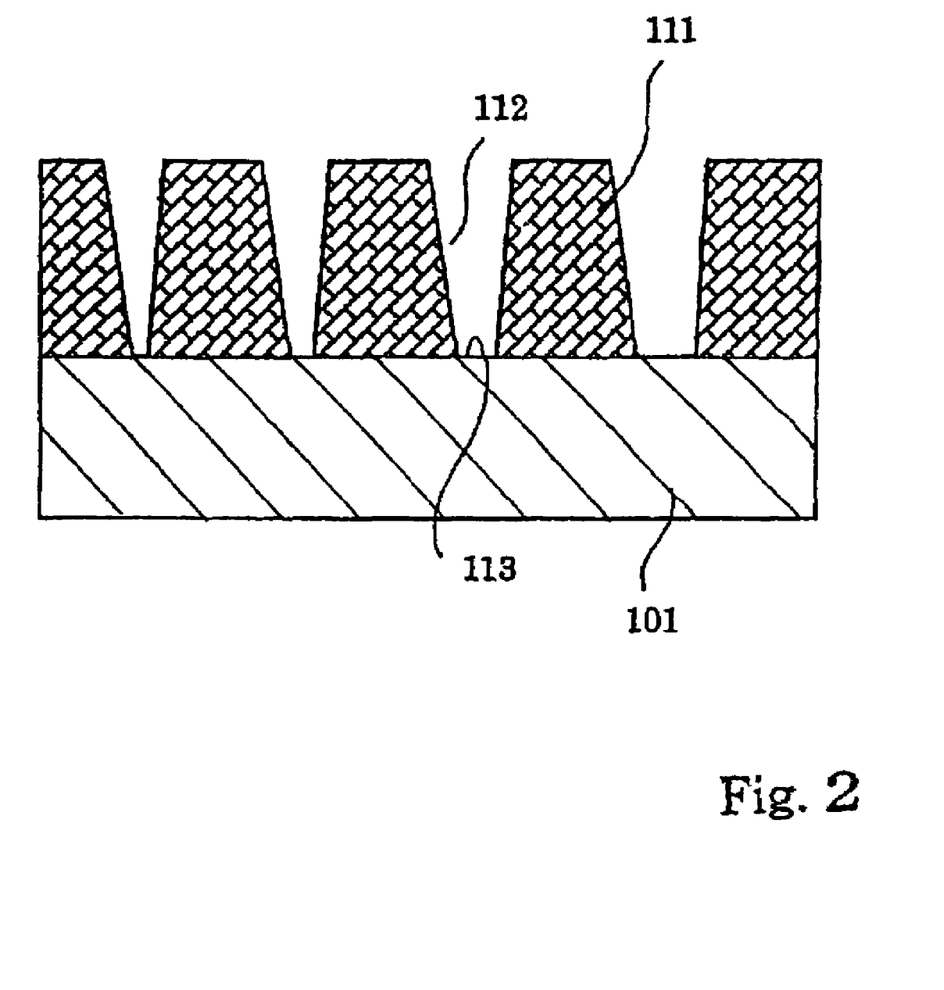
FIG. 2 is a cross sectional view showing the structure of a silicon wafer used in an experiment.

Silicon oxide was deposited over the entire surfaces of the silicon wafers by using a chemical vapor deposition, and the silicon oxide layers were 1000 nanometers thick. Photo-resist masks were formed on the silicon oxide layers through the photo-lithography, and the silicon oxide layers were selectively etched by using a dry etching technique. Recesses penetrated through the silicon oxide layers, and reached the major surfaces of the silicon wafers as shown in FIG. 2. The diameter of the recesses ranged from 0.25 microns to 3 microns. The recesses were 1000 nanometers deep. In FIG. 2, reference numerals 101 and 111 designate the silicon wafer and the silicon oxide layer, respectively. One of the recesses is labeled with reference numeral 112, and the bottom surface is designated by reference numeral 113. The photo-resist masks were ashed, and the silicon wafers 101 were cleaned through a series of cleaning/rinse techniques using the water solution containing sulfuric acid and hydrogen peroxide, water solution containing ammonia and hydrogen peroxide and pure water. Organic compound and alkaline metals were eliminated from the resultant structure shown in FIG. 2.

One of the silicon wafers was placed in a closed space where synthetic oil was vaporized. The silicon wafer was contaminated with the synthetic oil, i.e., hydrocarbon compounds. The other silicon wafer was stored in a clean atmosphere. The inventors used the silicon wafer contaminated with the hydrocarbon and the clean silicon wafer as the target substrate and the reference substrate, respectively.

The inventors further prepared a pair of silicon wafers. The silicon wafers were deposited with the silicon oxide, and the recesses were formed in the silicon oxide layers of 1000 nanometers thick. One of the silicon wafers was contaminated with the vapor of the synthetic oil, and the other was stored in the clean atmosphere. Thus, one of the silicon wafer was contaminated with the hydrocarbon compound as similar to the target substrate, and the other silicon wafer was kept clean as similar to the reference substrate. Thus, two pairs of silicon wafers were obtained.

Figure 3:
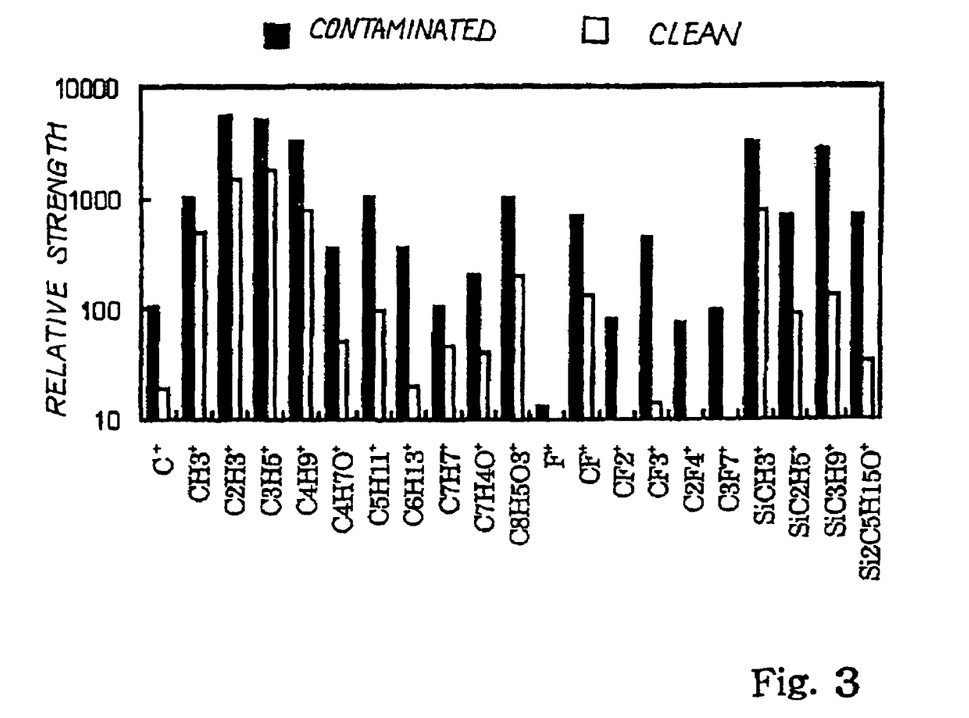
FIG. 3 is a graph showing the results of a time-flight secondary ion mass spectrometry.

The inventors firstly analyzed one of the two pairs of silicon wafers by using a time-flight secondary ion mass spectrometer. The contaminated silicon wafer and the clean silicon wafer were radiated with an ion beam. Then, the contaminants were scattered through the sputtering so as to analyze the contaminants directly. However, the surfaces of the silicon wafers were damaged due to the ion-bombardment. The ionic species were $Ga^+$, the accelerating energy was adjusted to 25 KeV. Ionic current was 1.2 pA, and the incident angle was 45 degrees. The mass spectrometry was carried out in the bunching-repetition mode at 10 KHz. An anti-static correction was not carried out. The analyzed region was 100 micron square. The results of the time-flight secondary ion mass spectrometry was shown in FIG. 3. Black columns and white columns stood for the relative strength on the contaminated silicon wafer and the relative strength on the clean silicon wafer, respectively.

Subsequently, the inventors placed the contaminated silicon wafer and clean silicon wafer of the other pair on the collecting electrode 108, and the target regions were successively aligned with the path for the electron beam 102 by controlling the movable stage 103. The electron beam 102 was radiated from the electron gun 104, and was accelerated in the electric field created by the anode 105. The acceleration energy was adjusted to 500 eV, and the beam current was 50 pA. The electron beam 102 was focused on the target region through the electron lens 107. Then, the electron beam 102 gave rise to the electron scattering phenomenon, and the electric charges lost the balance in the target region. In order to recover the balance, the current flew through the ampere meter 109, and the amount of current was accumulated for 200 millisecond.

The electron beam 102 accelerated at 500 eV gave rise to the electron scattering phenomenon in the surface portion of the silicon wafers of the order of several nanometers. However, the acceleration energy might be adjusted to a value between 1 eV and 500 eV depending upon the contaminated substrate. However, when clusters of tens nanometers to hundreds nanometers were predictable on the target region, the acceleration energy was adjusted to a value between 500 eV and 10000 eV. The beam current at 50 pA prevented the silicon wafers from charge-up phenomenon. The beam current between 1 pA and 50 pA was preferable from the view point against the charge-up phenomenon. However, if the beam current was increased between 50 pA and 1 nA, the signal-to-noise ratio was improved. The present inventors confirmed that the surface contamination was analyzed with the electron beam 102 at 1 eV-10000 eV at 1 pA-1 nA.

The electron beam 102 was regulable in the wide beam current range, i.e., 1 pA to 1 nA, and the lower limit, i.e., 1 pA was so small that the electron beam radiating unit 2 could make the electron beam 102 extremely narrow. The analyst precisely investigated the surface contamination over the target substrate with the extremely narrow electron beam 102 at a large signal-to-noise ratio. The present inventors confirmed that the contaminants in the bottom of a micro-hole less than 0.25 micron in diameter were analyzed by using the surface contamination analyzer according to the present invention. The upper limit of the acceleration energy was so large that the electron beam 102 could penetrate a thick silicon oxide layer, doped silicon oxide layer, silicon nitride layer and organic compound layers. The present inventors confirmed that the electron beam penetrated through a silicon oxide layer greater in thickness than 1000 nanometers.

The inventors investigated various substrates. The inventors deposited metal, i.e., aluminum and titanium or semiconductor, i.e., silicon-germanium and gallium arsenide over the silicon wafers, and further deposited silicon oxide over the metal/semiconductor layer. Micro-holes were formed in the silicon oxide layers, and the substrates were contaminated with the hydrocarbon compound. The inventors evaluated the surface contamination, and confirmed that the surface contamination was accurately evaluated by using the surface contamination analyzing technique described hereinbefore. This is because of the fact that the band gaps in the hydrocarbon compounds are different from those of the metal and those of the other kinds of semiconductor.

Figure 4:
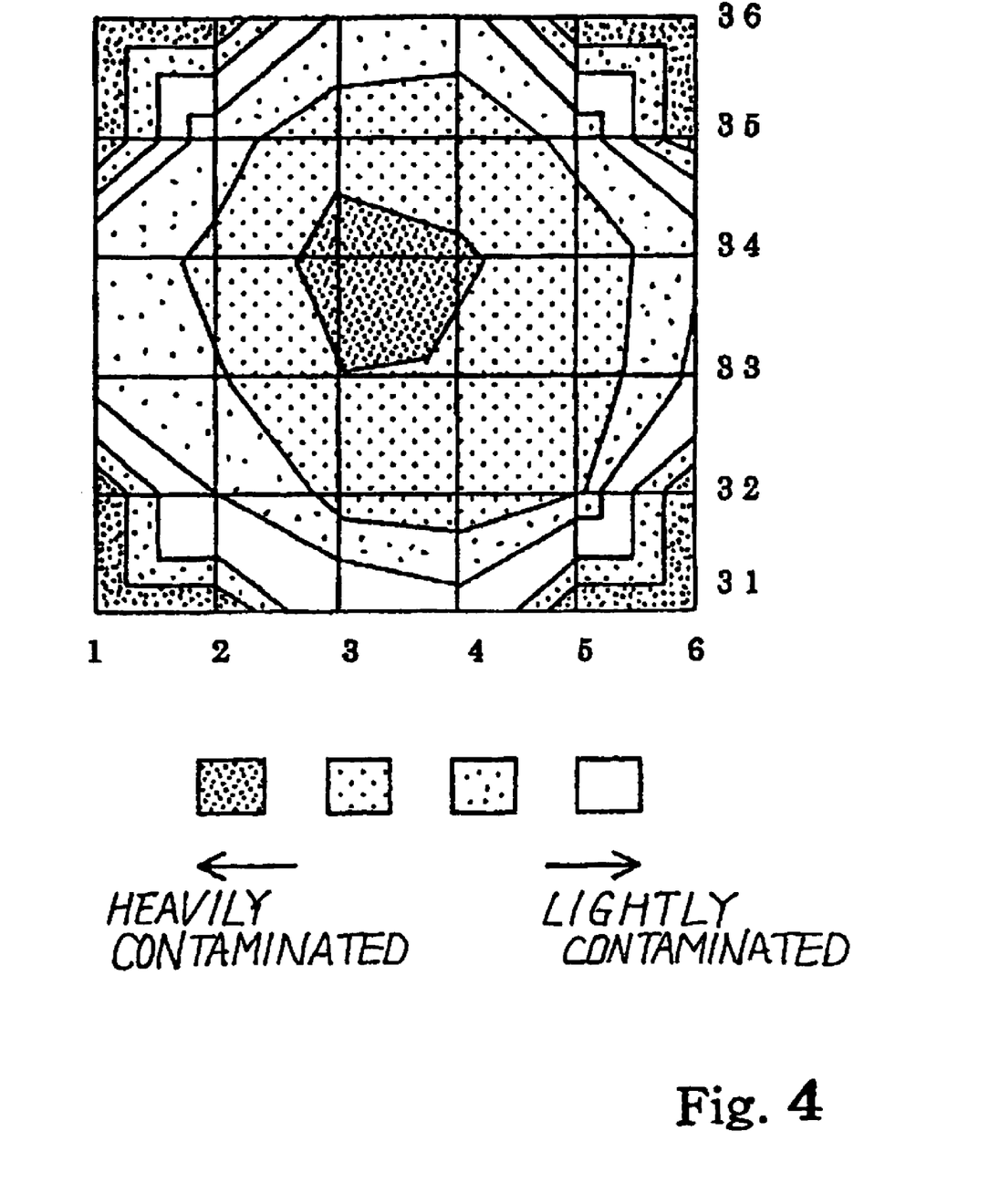
FIG. 4 is a graph showing a dispersion of contamination on a silicon wafer.

The inventors measured the accumulated current value over the major surfaces of the silicon wafers 101. The contaminants were dispersed over the major surface of the contaminated silicon wafer 101 as shown in FIG. 4. The central area and the corners was heavily contaminated, and the contamination became light toward the peripheral area. However, the peripheral area was locally contaminated. On the other hand, the dispersion was not observed in the clean silicon wafer. Accordingly, the accumulated current value was widely varied on the major surface of the contaminated silicon wafer, and the average current value was 1.58 pA. On the other hand, the accumulated current value was almost constant over the major surface of the clean silicon wafer, and the average current value was 2.03 pA. Thus, the contaminated silicon wafer was smaller in average current value than the clean silicon wafer. The inventors concluded that it was possible to evaluate the surface contamination with hydrocarbon on semiconductor wafers by comparing the average current value with that of the clean silicon wafer, i.e., the reference substrate without any damage to the silicon wafers.

If the contaminated region have been known, the analyst directly aligns the contaminated region with the electron beam path. However, if the contaminated region is unknown, the analyst stepwise aligns narrow regions with the electron beam path, and repeats the electron beam radiation and measurement of the current at each point. When the entire surface of the target substrate was radiated with the electron beam, the analyst can obtain a dispersion of the contamination over the entire surface on the basis of variation of measured current value.

As will be appreciated from the foregoing description, the electron beam is radiated onto a narrow region on the major surface of the target substrate so that the inelastic scattering takes place in the radiated region. The scattering phenomenon gives rise to current, and the amount of current is dependent on the substance in the radiated region, because conductive material, semiconductor material and insulating material have each band gaps different from one another. The surface contamination analysis according to the present invention is carried out on the basis of the difference in current. The amount of current flowing out from the target substrate is measured for a certain time period, and the substance is specified on the basis of the accumulated current value.

There is not any limit on the incident angle of the electron beam. This means that, even if a deep hole with a large aspect ratio is formed in the target region, the electron beam can reach the bottom of the deep hole. Thus, the surface contamination in the deep hole is analyzable through the surface contamination analyzing technique according to the present invention at a large signal-to-noise ratio.

Moreover, the electron beam is focused on an extremely narrow region in so far as the electron beam current is fallen within the wide range, i.e., 1 pA to 1 nA. This means that the target substrate is precisely analyzed by using the surface contamination analyzing technique at a large signal-to-noise ratio. Thus, the surface contamination analysis according to the present invention is advantageous over the prior art surface contamination analyzing techniques.

Second Embodiment

Figure 5:
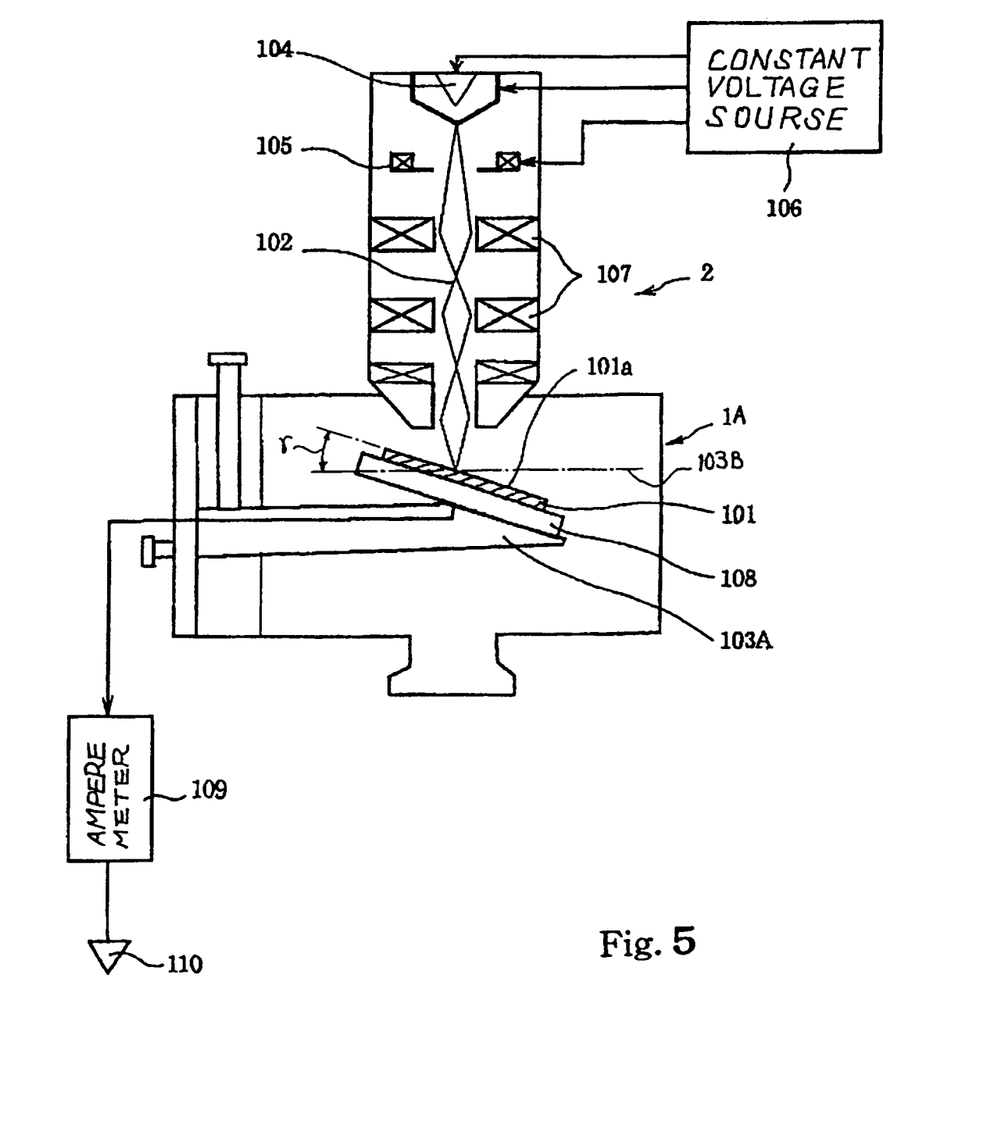
FIG. 5 is a schematic view showing the arrangement of another surface contamination analyzer according to the present invention.

Turning to FIG. 5 of the drawings, another surface contamination analyzer embodying the present invention also comprises a current measuring unit 1A and the electron beam radiating unit 2, which is similar in structure to the electron beam radiating unit incorporated in the first embodiment. Component parts of the electron beam radiating unit 2 are labeled with references designating the corresponding component parts of the first embodiment without detailed description.

The current measuring unit 1A is similar in structure to the current measuring unit 1 except a movable stage 103A. Although the movable stage 103 is two-dimensionally moved on a virtual plane 103 perpendicular to the electron beam 102, the movable stage 103A is inclined from the virtual plane 103B as well as the two-dimensional motion on the virtual plane 103B. In other words, the movable stage 103A varies the angle γ between the virtual plane 103B and the major surface of the target substrate 101.

The surface contamination analysis basically advances as similar to the first embodiment. A difference from the surface contamination analysis implementing the first embodiment is that the electron beam radiation is repeated by changing the incident angle.

The surface contamination analysis starts with preparation of a clean substrate and a contaminated substrate. Each of the clean/contaminated substrates is placed on the collecting electrode 108 on the movable stage 103A, and the current flowing into the ground 110 is measured for specifying the substance of the target region. If the target region has been already known, the movable stage 103A directly aligns the target region with the path of the electron beam 102, and the electron beam radiating unit 2 radiates the electron beam onto the target region. The current flows through the ampere meter 109, and the amount of current is measured for a certain time period. The movable stage 103A changes the angle γ, and the target region is radiated with the electron beam 102 at different incident angle. The current is measured for the certain time period. The electron beam radiation and the measurement are repeated at different incident angles.

Figure 6:
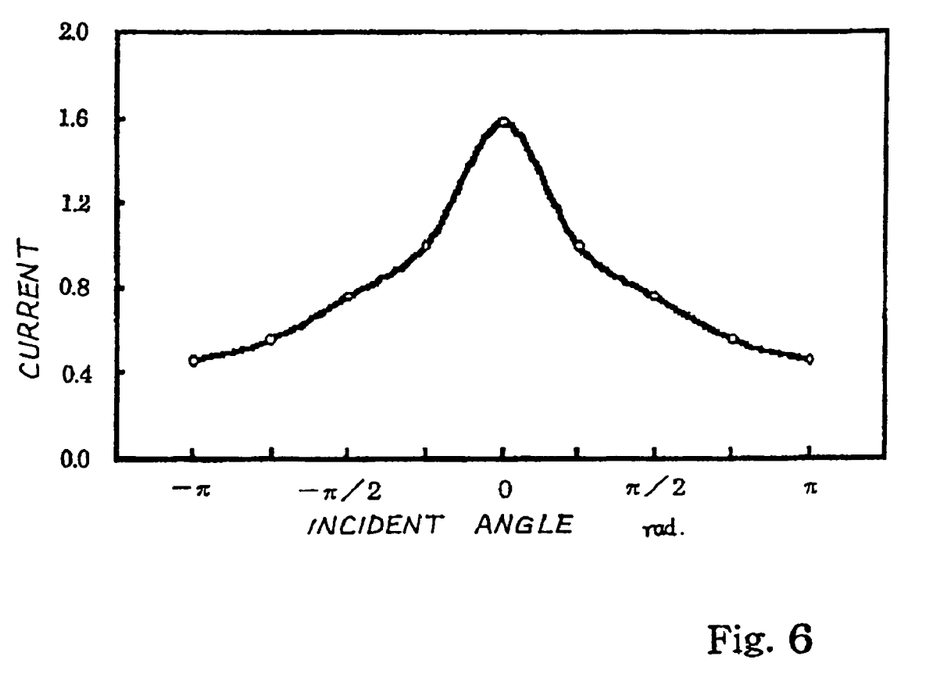
FIG. 6 is a graph showing the relation between the incident angle of an electron beam and the amount of current measured.

The inventors prepared the silicon wafers 101 formed with the recesses 112, and the recess 112 was aligned with the path of the electron beam 102 (see FIG. 2). The inventors adjusted the acceleration energy and the electron beam current to 500 eV and 50 pA, respectively, and the current was measured for 200 millisecond. The incident angle was stepwise varied from —π radian to π radian, and the amount of current measured at different incident angles was plotted as shown in FIG. 6. The amount of current was maximized at 0 radian., i.e., normal to the major surface, because the electron beam 102 reaches the bottom 113 of the recess 112. The amount of current was reduced together with the incident angle. Thus, the amount of current exhibited angle dependency.

The profile representative of the angle dependency was available for the three-dimensional contamination analysis. When the silicon wafer contaminated with the vapor of synthetic oil was radiated with the electron beam 102 at different incident angle, the profile representative of the angle dependency was different from the profile shown in FIG. 6 depending upon the surface contaminated with the hydrocarbon compounds. The inventors investigated the surface contamination after the dry etching on the silicon oxide layer 111. The residual hydrogen fluoride and hydrocarbon compound were left on the bottom surface of the recess 112. In the surface contamination analysis, the electron beam radiated at 0 radian reached the bottom 113 of the recess 112, and the contaminants was influential in the amount of current. However, the electron beam 102 obliquely radiated passed over the contaminants, and the amount of current was free from the contaminants. Thus, the profile was locally deformed, and the locally deformed profile exhibited the three-dimensional dispersion of the contaminants. The inventors concluded that the contamination was three-dimensionally analyzable by using the surface contamination analyzer implementing the second embodiment.

Third Embodiment

The surface contamination analysis implementing the third embodiment comprises the step of treating a semiconductor wafer or target substrate with heat in inert atmosphere at a predetermined temperature and the step for measuring the current flowing out from the semiconductor wafer under the electron beam radiation. These steps may be repeated. The surface contamination analyzer shown in FIG. 1 or 5 is used in the second step.

The inventors prepared a contaminated silicon wafer. The contaminated silicon wafers was placed on the movable stage 103A, and the target region was aligned with the path of the electron beam 102. The acceleration energy was 500 eV, and the electron beam current was 50 pA. The electron beam 102 was radiated from the electron gun 104 through the electron lens 107 onto the target region. The electron beam 102 gave rise to the electron scattering in the target region, and the current flew out from the target region. The amount of current was measured, and the accumulation time was 200 millisecond. The current was 1.61 pA.

Subsequently, the contaminated silicon wafer was placed in nitrogen atmosphere created in a chamber of a furnace. The nitrogen atmosphere was 70 degrees in centigrade, and the contaminated silicon wafer was treated with heat for 1 minute. The inventors repeated the measurement. The amount of current was 1.76 pA.

The contaminated silicon wafer was placed in the nitrogen atmosphere at 70 degrees in centigrade, again, and the temperature was increased to 200 degrees in centigrade at 30 degrees in centigrade per minute. The contaminated silicon wafer was kept in the high temperature nitrogen atmosphere for 1 minute. The inventors took out the contaminated silicon wafer from the furnace, and measured the current under the electron beam radiation. The current was increased to 1.89 pA.

The inventors put the contaminated silicon wafer into the high temperature nitrogen atmosphere at 200 degrees in centigrade, and raised the temperature at 10 degrees in centigrade per minute. When the nitrogen atmosphere reached 300 degrees in centigrade, the inventors stopped the temperature rise, and kept the contaminated silicon wafer in the high temperature nitrogen atmosphere at 300 degrees in centigrade for one minute. The inventors took out the contaminated silicon wafer from the chamber, and measured the current under the electron beam radiation. The current was increased to 2.07 pA.

The increase of the current was derived from the evaporation of certain contaminants. Some contaminants were evaporated at 70 degrees in centigrade, and several contaminants were evaporated at 200 degrees in centigrade. Other contaminants were evaporated at 300 degrees in centigrade. Thus, the contaminated silicon wafer was stepwise cleaned, and the amount of current was increased. The difference in measured current was unique to the contaminants removed from the contaminated silicon wafer. Thus, the contaminants were specified on the basis of the different in current measured after the heat treatment at a certain temperature.

The stepwise evaporation may be available for the surface contamination analysis from another point of view. An analyst is assumed to specify a contaminant. The analyst places the contaminated substrate in inert atmosphere, and heats the contaminated silicon wafer to the evaporation temperature of the known contaminant. The known contaminant is removed from the contaminated substrate, and the next analysis becomes simple.

Fourth Embodiment

In yet another surface contamination analysis embodying the present invention, the electron beam radiation is repeated under different conditions. The surface contamination analyzer shown in FIG. 1 or 5 is available for the surface contamination analysis implementing the fourth embodiment.

The inventors prepared a contaminated silicon wafer, and placed it on the collecting electrode 108. A target region was aligned with the path of the electron beam 102, and the electron beam 102 was radiated onto the target region at 500 eV at 50 pA. The current flew out from the target region, and the inventors measured the amount of current. The current was 1.60 pA.

Subsequently, the inventors adjusted the acceleration energy to 1000 eV, and the measured the current under the electron beam radiation at 50 pA. The amount of current was 2.24 pA. The inventors further increased the acceleration energy to 1500 eV, and measured the current under the electron beam radiation at 50 pA. The amount of current was increased to 3.48 pA. Thus, the amount of current was varied together with the acceleration energy.

Figure 7:
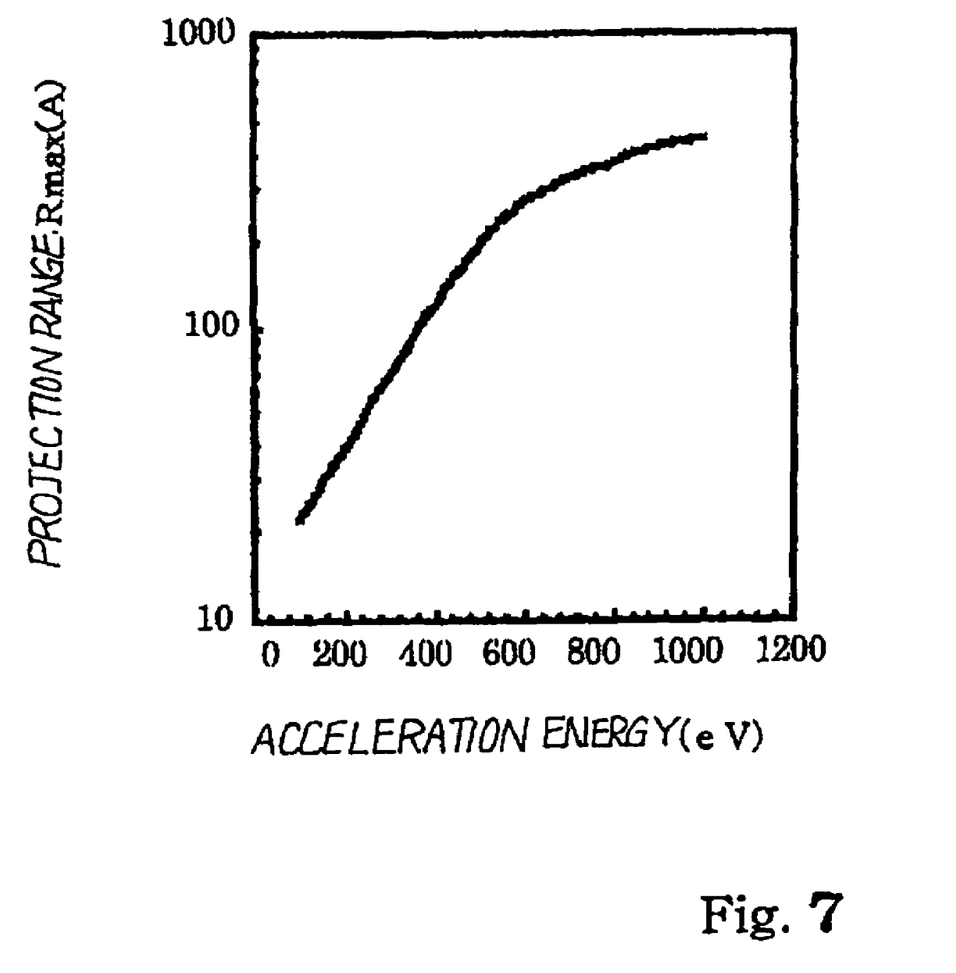
FIG. 7 is a graph showing the relation between the acceleration energy of an electron beam and the projection range of electrons.

FIG. 7 shows a relation between the acceleration energy and the projection range of implanted electrons. The stronger the acceleration energy, the longer the projection range. The implanted electron beam causes the inelastic scattering to take place, and the inelastic scattering gives rise to the generation of the current flowing out from the region therearound. When the electron beam 102 reaches the deep region, the electrons are generated through the scattering more than those generated by the electron beam terminated at a shallow region. When a large organic compound cluster of tens nanometers to hundreds nanometers exists in the target region, the electron beam 102 is terminated at a certain region in the large cluster in so far as the acceleration energy is weak. However, the electron beam reaches a deeper portion together with the increase of acceleration energy, and finally, reaches the silicon wafer. Accordingly, the amount of current was continuously increased in the large organic compound cluster, and is drastically varied at the boundary between the large organic cluster and the silicon wafer. The analyst can determine the size of the large organic compound cluster on the basis of the acceleration energy at the drastic change.

Contribution To Fabrication Process

If a contaminated semiconductor wafer is conveyed from one apparatus to another, the contaminants are also carried to the next stage, and the contamination is spread over the fabrication system. In order to prevent the fabrication system from the contamination, it is necessary to evaluate the surface contamination of silicon wafers. If the contamination is serious, the silicon wafer is to be cleaned.

Figure 8:
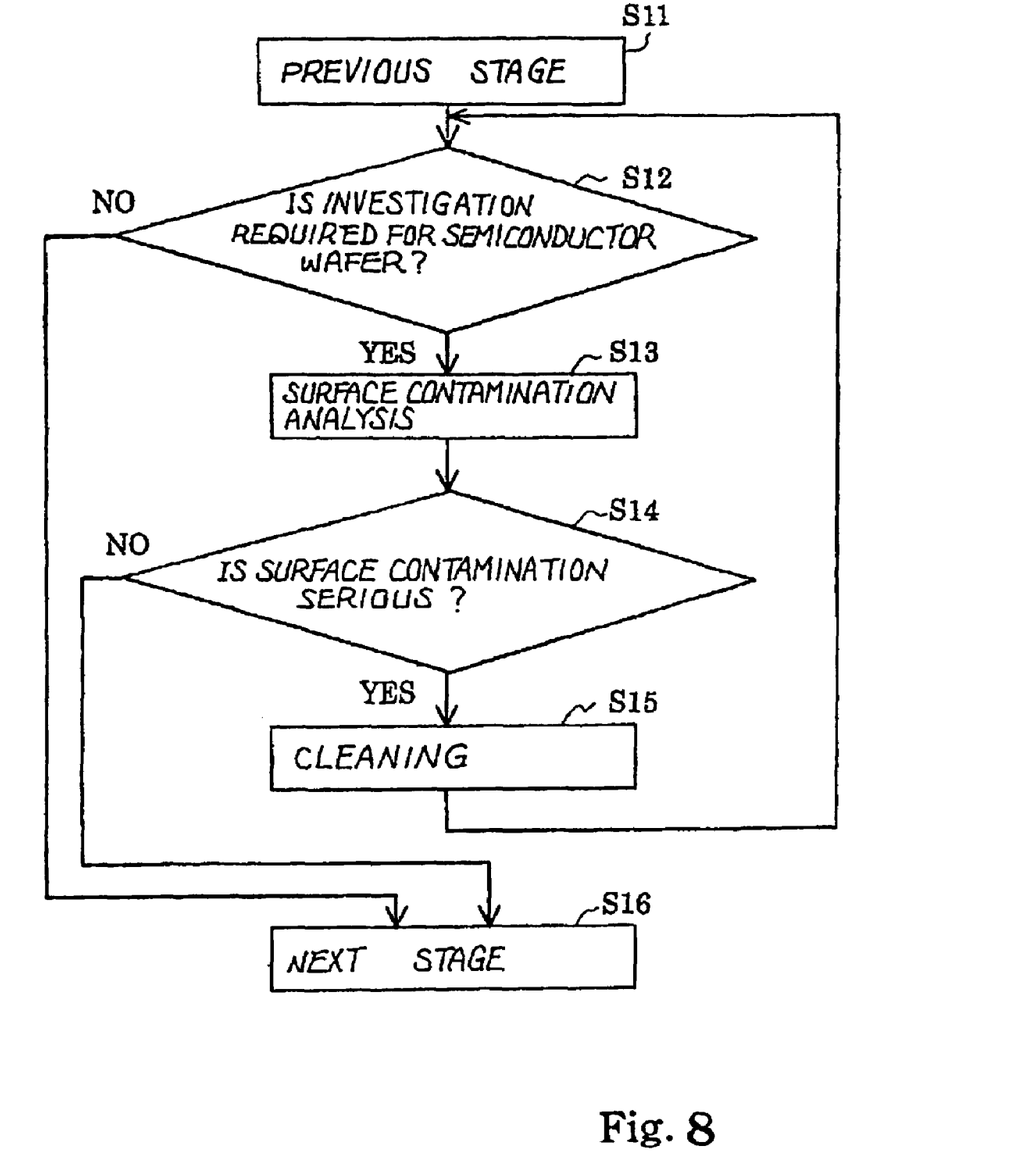
FIG. 8 is a flowchart showing a process sequence containing the surface contamination analysis according to the present invention.

FIG. 8 shows a process for fabricating semiconductor devices, and the surface contamination analysis according to the present invention is incorporated in the process. The process may be categorized in a single wafer processing.

A cleaning, drying, etching, photo-resist removal, ion-implantation or ashing is, by way of example, carried out at step S11. The cleaning means a wet cleaning, which may be carried out in water solution containing sulfuric acid and hydrogen peroxide which is abbreviated as "SPM", water solution containing ammonia and hydrogen peroxide which is abbreviated "APM or SC-1", diluted hydrofluoric acid which is abbreviated as "DHF", brush-scrubbing, hydrogen-containing water and ozone-containing water. The wet cleaning may be assisted with megasonic or ultrasonic. When the previous stage is completed, the manufacturer makes a decision whether or not the semiconductor wafer is to be investigated for the surface contamination as by step S12. If surface contamination is predicted, the answer is given affirmative, and the surface contamination analysis is carried out as by step S13. On the other hand, there is not any serious contamination source in the previous stages. The answer at step S12 is given negative, and the manufacturer decides the process to proceed to the next stage at step S16. A heat treatment, thin film growth, deposition, ion-implantation, dry etching or photolithography is carried out in the next stage.

The manufacture is assumed to decide the semiconductor wafer to be investigated at step S12. The semiconductor wafer is subjected to the surface contamination analysis. The semiconductor wafer is put on the movable stage 103/103A, and a target region is aligned with the path of the electron beam 102. The electron beam 102 is radiated onto the target region at a predetermined acceleration energy and at a predetermined beam current. The scattering takes place, and gives rise to generation of current flowing out from the target region. The current value is accumulated for a predetermined time period. The semiconductor wafer may be inclined so as to repeat the electron beam radiation at different angles. The movable stage 103/103A makes the next target region aligned with the path of the electron beam 102, and the electron beam radiation is repeated so as to measure the current. When the current is measured in all of the target regions or entire surface of the semi-conductor wafer, the analyst proceeds to step S14.

The analyst checks the accumulated current values to see whether or not the degree of contamination exceeds a critical value as by step S14. First, the accumulated current values are subtracted from accumulated current values measured in a reference semiconductor wafer, and the differences are absolutized. The absolute values are representative of the degree of contamination. The absolute values are compared with a margin to be allowed in the next stage, i.e., the critical value. The margin has been experimentally determined. If the absolute values are less than the margin, the answer at step S14 is given negative, and the manufacturer proceeds to the next stage. On the other hand, when the absolute values are equal to or greater than the margin, the surface contamination is serious, and the answer at step S14 is given affirmative.

The manufacturer proceeds to step S14, and the semiconductor wafer is cleaned through an appropriate cleaning technique so as to remove the contamination from the semiconductor wafer.

EXAMPLES

The inventors investigated the effects of the fabrication process containing the surface contamination analysis. The inventors prepared two 8-inch silicon wafers. Silicon oxide was thermally grown to 10 nanometers thick on the major surfaces of the silicon wafers, and, thereafter, the two silicon wafers were left in the clean room for a week. One of the silicon wafers, i.e. the first silicon wafer was assumed that the negative answer was given at step S12, and the other silicon wafer, i.e., the second silicon wafer was assumed that the positive answer was given at step S12.

The second silicon wafer was investigated at step S13. The surface contamination was serious, and the answer at step S14 was given affirmative. With the positive answer at step S14, the second silicon wafer was cleaned through a series of cleaning steps using water solution containing sulfuric acid and hydrogen peroxide, water solution containing ammonia and hydrogen peroxide and diluted hydrofluoric acid, and, thereafter, the second silicon wafer was rinsed in pure water.

The inventors evaluated the first silicon wafer and the second silicon wafer by using FT-IR method. The contaminants on the second silicon wafer were $CH_2$ at $0.5 \times 10^{14}$ molecules/$cm^2$ and $CH_3$ at $0.13 \times 10^{14}$ molecules/$cm^2$ after step S15. On the other hand, the first silicon wafer was not subjected to neither surface contamination analysis at step S13 nor cleaning at step S15, and the contaminants on the first silicon wafer were $10\times10^{14}$ molecules/cm$^2$ and CH$_3$ at $1.1\times10^{14}$ molecules/cm$^2$. The present inventors confirmed that the surface contamination analysis followed by the cleaning was effective against the spread of the contaminants over the fabrication system. Only the seriously contaminated silicon wafers were cleaned so that the surface contamination analysis according to the present invention is economical.

The inventors selectively carried out the cleaning by using the megasonic, the cleaning in the ozone-containing wafer, the cleaning in the hydrogen-containing water and the brush-scrub cleaning at step S15, and confirmed that the silicon wafers were decontaminated. The inventors concluded that the manufacturer was to select any cleaning method appropriate to the predicted contaminants.

Figure 9:
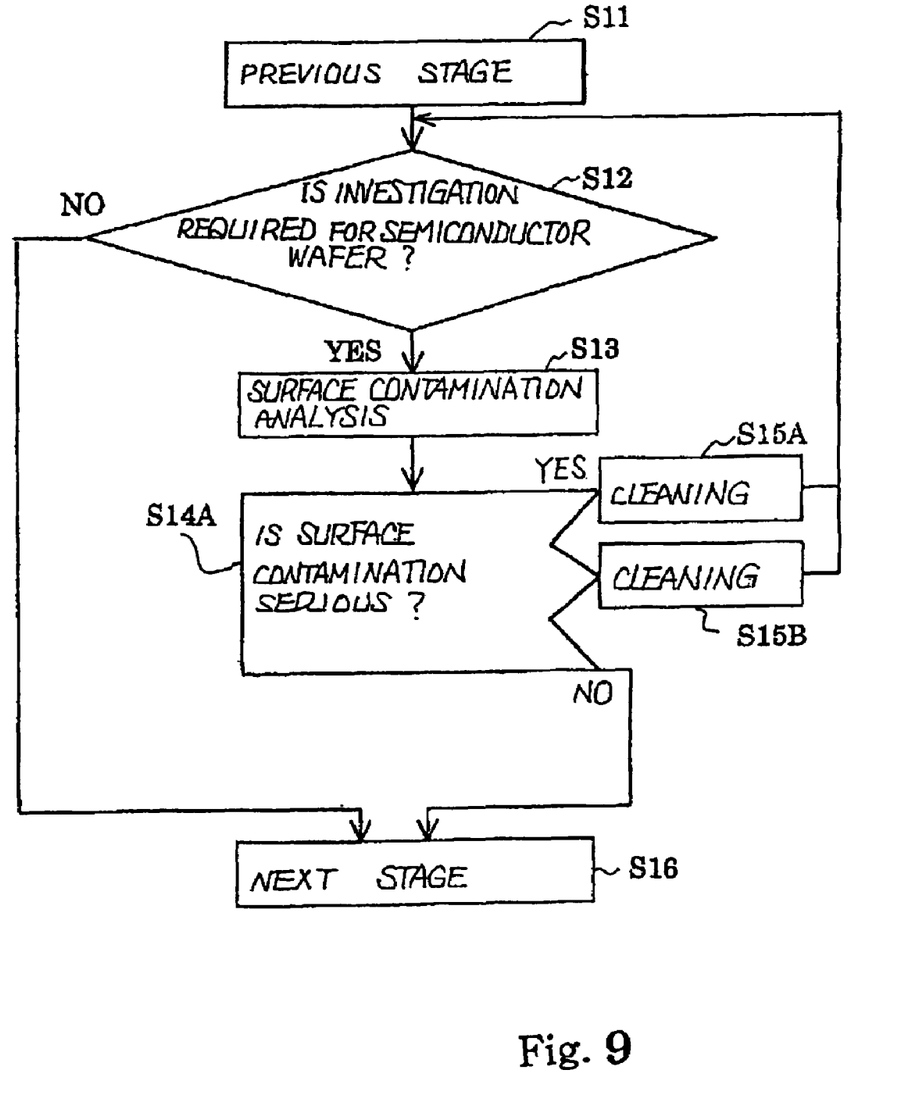
FIG. 9 is a flowchart showing another process sequence containing the surface contamination analysis according to the present invention.

Accordingly, the fabrication process is modified as shown in FIG. 9. In this instance, the analyst applies plural critical values to the absolute values of the differences. In this instance, the absolute values are compared with two critical values for two kinds of cleaning method. If the absolute values are closer to the first critical value than the second critical value, the manufacturer proceeds to step S15A. On the other hand, if the absolute values are closer to the second critical value than the first critical value, the manufacturer proceeds to step S15B. The first kind of cleaning method is, by way of example, different from the second kind of cleaning method in cleaner used therein, the concentration of the cleaner, cleaning temperature and time period to be consumed.

The accumulated current value is assumed to be fallen within the range between 2.0 pA and 2.5 pA under the conditions that the acceleration energy and the beam current are 500 eV and 30 pA. The manufacturer proceeds to the first cleaning S15A, and the silicon wafer is decontaminated in cleaning solution containing hydrofluoric acid and water at 1:100 at 22 degrees in centigrade for one minute. On the other hand, when the accumulated current value is fallen within the range equal to or greater than 1.8 pA and less than 2.0 pA, the silicon wafer is decontaminated in cleaning solution containing hydrofluoric acid HF, hydrogen peroxide H$_2$O$_2$ and water H$_2$O at 1:1:100 at 22 degrees in centigrade for 0.5 minute.

As will be appreciated from the foregoing description, the surface contamination analysis is based on the current flowing out from a target region under the electron beam radiation. Even if the target region has a complicated contour and is contaminated with plural contaminants, the degree of contamination is accurately decided without damage to the target region. The incident angle of the electron beam is variable so that the electron beam reaches the bottom of a micro-hole with a large aspect ratio. Moreover, the electron beam current is selectable in the wide range, and is focused on an extremely narrow region. Thus, the analyst precisely evaluates the surface contamination on a target substrate.

When the surface contamination analysis is introduced into a process for fabricating semiconductor devices, the manufacturer evaluates the semiconductor wafers at any point in the process sequence, and selectively decontaminates the seriously contaminated semiconductor wafers. Thus, the manufacturer prevents the fabrication system from the undesirable contaminants, and enhances the production yield and the reliability of products.

Although particular embodiments of the present invention have been shown and described, it will be apparent to those skilled in the art that various changes and modifications may be made without departing from the spirit and scope of the present invention.

For example, the accumulated current values at certain points in the fabrication system may be stored in certain files, respectively. In this instance, the analyst watches the variation of the accumulated current values at each point to see whether or not the fabrication apparatus at the previous stage is troubled. If the accumulated current values at the certain point, the analyst predicts the trouble for trouble shooting. Even tough there are plural steps until the certain point, the analyst specifies the apparatus in trouble on the basis of the characteristic patterns of the accumulated current values.

What is claimed is:

1. A method for investigating contamination of a target region of a semiconductor wafer, the method comprising:
   irradiating the target region with an electron beam;
   measuring the amount of current generated from the semiconductor wafer in response to the irradiating the target region with the electron beam; and
   comparing the amount of current generated in response to the irradiating of the electron beam with a reference current to determine a difference therebetween to detect one or more contaminates on or in the target region.

2. The method of claim 1 wherein the reference current is generated in response to irradiating a region of a reference wafer with an electron beam.

3. The method of claim 1 further including determining a degree of contamination on or in the target region using (1) the amount of current generated in response to the irradiating of the electron beam and (2) the reference current.

4. The method of claim 1 further including generating a three-dimensional representation of the degree of contamination using (1) the amount of current generated in response to the irradiating of the electron beam and (2) the reference current.

5. The method of claim 1 wherein measuring the amount of current generated in response to irradiating the target region with the electron beam includes:
   irradiating the target region with the electron beam at a first incident angle;
   measuring the amount of current generated in response to the irradiating the target region with the electron beam at the first incident angle;
   irradiating the target region with the electron beam at a second incident angle; and
   measuring the amount of current generated in response to the irradiating of the electron beam at the second incident angle.

6. The method of claim 5 further including determining a degree of contamination on or in the target region using (1) the amount of current generated in response to the irradiating of the electron beam at the first incident angle and (2) the amount of a current generated in response to the irradiating of the electron beam at the second incident angle.

7. The method of claim 5 further including generating a three-dimensional representation of the degree of contamination using the amount of current generated in response to the irradiating of the electron beam at the first and second incident angles.

8. The method of claim 1 further including removing at least one contaminant from the target region after detecting at least one contaminant on or in the target region.

9. The method of claim 1 further including evaporating at least one contaminant from the target region after detecting the at least one contaminant on or in the target region.

10. The method of claim 1 further including: heat treating the wafer to remove at least one contaminant on or in the target region; and thereafter, irradiating the target region with the electron beam; and measuring the amount of current generated in response to the irradiating of the electron beam.

11. The method of claim 1 further including: measuring the amount of current generated in response to the irradiating the target region with the electron beam when the wafer is at a first temperature; and measuring the amount of current generated in response to the irradiating the target region with the electron beam when the wafer is at a second temperature.

12. The method of claim 11 further including detecting a difference between the amount of current generated in response to irradiating the target area with the electron beam at the first temperature and the amount of current generated in response to irradiating the target area with the electron beam at the second temperature.

13. The method of claim 12 further including generating a three-dimensional representation of a degree of contamination using the amount of current generated in response to the irradiating of the electron beam at the first and second temperatures.

* * * * *